United States Patent

Schneider et al.

[11] Patent Number: 5,407,886
[45] Date of Patent: Apr. 18, 1995

[54] MOLDED CATALYST BODY

[75] Inventors: Michael Schneider, Ottobrunn; Karl Kochloefl, Bruckmühl/Heufeld; Gerhardt Maletz, Bruckmühl, all of Germany

[73] Assignee: Sud-Chemie Aktiengesellschaft, Munich, Germany

[21] Appl. No.: 200,585

[22] Filed: Feb. 22, 1994

Related U.S. Application Data

[63] Continuation of Ser. No. 994,199, Dec. 21, 1992, abandoned.

[30] Foreign Application Priority Data

Dec. 23, 1991 [DE] Germany ............... 41 42 897.8

[51] Int. Cl.$^6$ ............................................. B01J 23/70
[52] U.S. Cl. ........................................ 502/244; 502/258; 502/259; 502/260; 502/337; 502/338; 502/345
[58] Field of Search ............... 502/244, 258, 259, 260, 502/337, 338, 345

[56] References Cited

U.S. PATENT DOCUMENTS

| | | | |
|---|---|---|---|
| 3,652,458 | 3/1972 | Gobron et al. | 502/244 |
| 3,668,148 | 6/1972 | Van Beek | 252/440 |
| 3,673,115 | 6/1972 | Linsen et al. | 502/259 |
| 3,988,263 | 10/1976 | Hansford | 502/337 |
| 4,142,962 | 3/1979 | Yates | 208/109 |
| 4,184,982 | 1/1980 | Schroeder et al. | 502/244 X |
| 4,490,480 | 12/1984 | Lok | 502/315 |
| 4,503,092 | 3/1985 | Klebe | 427/213 |
| 4,666,635 | 5/1987 | Klimmek | 260/409 |
| 4,670,416 | 6/1987 | Klimmek | 502/259 |
| 4,695,560 | 9/1987 | Gattuso | 502/222 |
| 4,716,256 | 12/1987 | Johnson | 585/274 |
| 5,073,661 | 12/1991 | Scheffer | 585/640 |
| 5,155,084 | 10/1992 | Horn | 502/252 |

FOREIGN PATENT DOCUMENTS

| | | |
|---|---|---|
| 510771 | 10/1992 | European Pat. Off. . |
| 2523869 | 9/1983 | France . |
| 459247 | 3/1975 | U.S.S.R. . |

*Primary Examiner*—Asok Pal
*Assistant Examiner*—Timothy Howard Meeks
*Attorney, Agent, or Firm*—Scott R. Cox

[57] ABSTRACT

A molded catalyst body that contains in a reduced state a metal of the ferrous group and/or copper on a support and is characterized by the following features:

(a) Metal content: about 5 to about 40 weight percent, based on the total weight of the catalyst;
(b) Metal-crystal size: $\leq 3$ nm;
(c) Volume of the pores with a diameter of 7.5 nm to 15 μm: 0.05 to 0.9 ml/g catalyst;
(d) BET surface area: 80–400 m$^2$/g catalyst;
(e) Fracture strength: >30N (based on cylindrical molded body with a diameter of 1.5 mm and a length of 5 mm);
(f) Bulk density: 250–350 g/l.

24 Claims, No Drawings

MOLDED CATALYST BODY

This is a continuation of application Ser. No. 07/994,199, filed on Dec. 21, 1992, now abandoned.

BACKGROUND OF THE INVENTION

The field of art to which this invention is directed is catalysts for hydrogenation of hydrocarbons, and for methanization and oligomerization processes.

Metal catalysts based on Fe, Co, Ni and Cu are already used in hydrogenation of hydrocarbons and in methanization and oligomerization processes. A high specific surface area of the metal is important for the catalyst activity. This is achieved, for example, by means of high metal loading, but this results in relatively large metal crystals. Very small metal crystals are obtained only when using very small quantities of metal on the support. The resulting specific metal surface area is therefore usually less than that of catalysts with a high load and large crystals.

A method of obtaining crystal sizes in the range of <2.5 nm even with loads of, for example, 25 wt % MeO (where Me stands for a ferrous metal or copper) on a support is the hydrolysis precipitation method described by Geus (*Prep. Catal. III*, 1 (1983)). This process starts with a powdered support suspended in a solution of metal nitrate and urea, for example. By thermal decomposition of the urea, the metal is deposited very homogeneously on the support and forms very small crystals in reduction. In this way, it is possible to obtain a specific metal surface area which is otherwise possible only with a high metal load. The resulting powdered catalyst has the disadvantage that it cannot be processed to yield molded bodies without using large quantities of inorganic binders. However, this greatly reduces the active component content which in turn leads to a definite sacrifice in terms of activity.

There have been attempts to produce molded metal catalysts with a high metal dispersion by means of precipitation on preshaped supports according to the hydrolysis method. Studies in this regard have already been conducted by K. F. de Jong (*Prep. Catal V.*, 385 (1990)), although Mn and Mo were used. $SiO_2$ beads (diameter up to 1.5 mm) were introduced into a very dilute solution of the metal nitrates and urea and the metals were deposited on them by decomposing the urea. The disadvantage of this method is that only a very low metal load (up to 5%) can be achieved. At higher concentrations, some of the metal is precipitated as $Me(OH)_2$ in the solution. U.S. Pat. No. 3,668,148 describes this process for precipitation of nickel, but it has the disadvantage that half of the starting nickel remains in solution.

USSR Inventor's Certificate A 459,247 discloses a process for producing nickel catalysts for hydrogenation of organic compounds and for fine gas purification, whereby the nickel is precipitated from solutions of nickel salts on suspended silica gel by means of an aqueous ammonium hydroxide solution or ammonium carbonate solution. Precipitation is performed at a temperature of 70° C. to 75° C. and a pH of 5 to 7.5. The precipitate is aged in the mother liquor for 1.5 to 2 hours at 90° C. to 95° C. After filtering, washing and drying, the precipitate is calcined and reduced in a stream of hydrogen. The catalysts have a nickel content of 10 to 50 wt %. The BET surface of the support is between 55 and 300 $m^2/g$, and the nickel surface amounts to between 18 and 28 $m^2/g$ of the catalyst. Although it is stated that the catalysts produced in this way are tablets measuring 5×5 mm, no information is provided regarding the strength of these tablets, or how catalyst bodies with an increased strength can be obtained. Furthermore, no information is given regarding the size of the nickel crystals or the pore volume.

French Patent A 2,523,869 describes an oligomerization catalyst based on monovalent nickel on a silicic acid support that is produced by treating the silicic acid support with an aqueous alkali or ammonium salt solution having a pH of more than about 10 and then treating the silicic acid that has been pretreated in this way with an aqueous nickel(II) salt solution at a pH of about 8 in order to replace the alkali or ammonium ions bound by the silicic acid with nickel ions. Then the resulting product is heated to 300° C. to 900° C. and the divalent nickel is reduced to monovalent nickel. Thus, the nickel is not in the form of a metal so no statements can be made regarding the size of the metal crystals.

U.S. Pat. No. 4,716,256 discloses a process for selective hydrogenation of diolefins to monoolefins whereby a catalyst that consists essentially of elemental nickel on an inorganic support is used. The catalyst may contain 1 to 40 wt % metallic nickel, preferably 2 to 20 wt % metallic nickel, with 5 to 10 wt % being most preferred. However, no information is provided regarding the other properties of the catalyst.

European Patent B 307,520 describes a hydrogenation catalyst consisting of an aluminum oxide support material, 0.05 to 1.5 wt % sulfur and 1.0 to 25 wt % nickel. The aluminum oxide support material has a pore volume of 1 to 3 $cm^3/g$ and a surface area of more than 150 $m^2/g$, whereby less than 25% of the total pore volume is formed by pores having a pore diameter of less than 15 nm and more than 60% of the pore volume is formed by pores whose diameter is more than 60 nm. The catalyst may be in the form of pellets, beads, extrudates or irregularly shaped bodies, but no information is given regarding the strength of the catalyst. Furthermore, no information is given regarding the size of the nickel crystals.

U.S. Pat. No. 3,668,148 discloses a process for production of metal catalysts on a particulate support whereby the support particles are suspended in an aqueous solution of a salt of the catalyst metal and a substance that releases hydroxyl ions when heated in aqueous solution. The suspension is heated to a temperature of more than 100° C. in an autoclave, whereupon the particles of the catalyst metal are uniformly deposited on the support particles. The catalyst is reduced in the usual way. A number of catalyst metals are described, and metals of the ferrous group and copper are also mentioned. However, no statements are made regarding the pore volume or the formation of molded bodies.

There is a need to obtain catalysts having a high metal load on porous molded bodies without any loss of metal that would also have sufficient strength and high specific pore volume even without the use of binders.

SUMMARY OF THE INVENTION

This invention is directed to porous molded catalyst bodies containing in a reduced state a metal of the ferrous group and/or copper on a support.

The catalysts of this invention are characterized by the following features:
(a) Metal content: about 5 to about 40 wt %, based on total weight of the catalyst;

(b) Metal crystal size: $\leq 3$ nm;
(c) Volume of pores having a diameter of 7.5 nm to 15 $\mu$m: about 0.05 to about 09.9 ml/g of catalyst;
(d) BET surface area: 80–400 m$^2$/g catalyst;
(e) Fracture strength: >about 30N (based on a cylindrical molded body with a diameter of 1.5 mm and a length of 5 mm;
(f) Bulk density: about 250 to about 350 g/liter.

The support is preferably made of a powdered oxide or silicate, most preferably pyrogenic silicic acid.

The pore diameter distribution of the catalysts is as follows:
7.5 nm to 14 nm: 0 to 2%
14 nm to 80 nm: 1 to 25%
80 nm to 1.75 $\mu$m: 50 to 90%
1.75 $\mu$m to 15 $\mu$m: 0 to 15%

DESCRIPTION OF THE INVENTION

The metal crystal size (feature (b)) is determined by measuring the most intense X-ray diffraction reflex of the metal, e.g., nickel, in a reduced state. For the measurements conducted as part of the present invention, a Philips model PW 1729 X-ray diffractometer was used. Of course, other X-ray diffractometers may also be used. The most intense reflex was analyzed with the help of the Voigt function as described by J. I. Langford, *J. Applied Crystall.*, Vol. 11, 10 (1978). This involves essentially determining the half-width of the most intense reflex.

The specific pore volume is determined according to the mercury penetration method described by J. van Brakel et al., *Powder Technology*, Vol. 29, 1 (1981). In this method, mercury is injected into the molded catalyst body at a pressure of up to about 2000 bar, and the reduction in volume of mercury is plotted as a function of the pressure. This yields a curve from which the pore distribution can be determined. Only the volume and distribution of pores with a diameter of >7.5 nm can be determined by the mercury penetration method. If the total pore volume is to be determined, the water uptake method according to DIN 51,056 is used. According to this method, a precisely weighted amount of molded catalyst body is covered with water at ambient temperature, which water has been boiled for at least 30 minutes. The excess water is removed from the molded bodies by filtration after 4 hours, and then the molded bodies are weighed again. The percentage weight increase corresponds to the water uptake, from which the total pore volume can then be calculated.

The BET surface area (feature d) is determined on the basis on the N$_2$ sorption according to the single-point method as described in DIN 66,132.

The fracture strength (feature e) is determined by using the 4M tablet tester from Schleuniger. A molded cylindrical body 5 mm long is placed between the jaws of the device and a pressure is exerted at right angles to the axis of the cylinder. The rate of increase in force is 20N/sec. The compressive strength is obtained from an average of 100 measurements.

The bulk density (feature f) is determined by filling a graduated cylinder with a diameter of 8 cm up to the one-liter mark with the catalyst molded bodies to be tested and then determining the weight of the molded bodies.

The catalyst molded bodies of this invention have a high metal load even though in producing them the insoluble metal compounds are not precipitated separately from the support bodies in the aqueous solution.

The molded catalyst bodies of this invention are obtained essentially by two variants. According to the first variant, the procedure is to react a compound that decomposes slowly on heating in solution with an increase in pH of the solution with a solution of a salt of a metal of the ferrous group and/or copper in the presence of a powdered suspended support in order to produce a precipitate of insoluble metal compound on the support. The precipitate is then removed from the solution together with the support and while still wet is plasticized while applying heat and then shaped, dried and/or calcined. The metal compound or the dried and/or calcined metal compound is then reduced.

According to the second variant, a compound that decomposes slowly when heated in solution with an increase in pH is reacted with a solution of a salt of a metal of the ferrous group and/or copper in the pores of a porous molded support body in order to produce a precipitate of insoluble metal compound in the pores of the molded support body. The precipitate is then separated from the solution together with the molded support body, dried and/or calcined, and the metal compound or the dried and/or calcined metal compound is reduced.

Compounds that will decompose slowly when heated in solution with an increase in pH include preferably ammonium carbonate or bicarbonate, urea, an amide such as formamide, dimethylformamide, acetamide, dimethylacetamide or an amine such as hexamethylenetetramine. The temperature at which the compounds decompose is >50° C., preferably >90° C.

The metal salt solution is preferably used in the form of a concentrated solution, and according to the second variant of the process, an extremely porous support with a water uptake capacity of at least 140% is used. In both variants of the process, the mixture is reacted with a compound that will decompose slowly when heated in solution with an increase in the pH of the solution and then is reacted at a temperature above the decomposition temperature of this compound, generally for several hours. The compound which decomposes slowly on heating with an increase in the pH of the solution is preferably used in a 1.5–3 molar excess. After precipitating the metal compound, its content calculated as MeO is between 5 and 40 wt %, while the support amounts to 60 to 95 wt %.

The solvent used in the process preferably has a boiling point higher than the decomposition temperature of the compound which decomposes with an increase in pH. Both this compound and the metal salt are soluble in the solvent. If urea is used according to a preferred embodiment of this invention, suitable solvents include, for example, water and/or ethylene glycol. Precipitation is initiated by decomposition of the compound which decomposes with an increase in pH at an elevated temperature and preferably takes place over a long period of time, especially a period of 4 to 60 hours. Then the solids are filtered out, washed and preferably transferred to a heatable mixer where they are adjusted to the moisture content required for shaping, preferably a dry solids content of between about 50% and about 70% while plasticizing at the same time. The resulting paste is processed to yield molded bodies, e.g., by agglomeration or extrusion. The catalysts are shaped into pressed cylinders, tablets, pellets, wagon wheels, rings, stars or extruded shapes such as solid extrudates, polylobed strands, hollow strands and honeycombs.

According to an especially preferred embodiment of this invention, the paste is extruded to yield strands with a diameter of $\geq 1.5$ mm and then dried. Drying preferably takes place first at a temperature of $\geq 95°$ C. for a period of $\geq 4$ hours. The dried molded bodies are either reduced immediately or first calcined, whereby calcination takes place at a temperature of $\geq 250°$ C., preferably 300° C. to 500° C. for a period of 2 to 10 hours.

Reduction preferably takes place at a temperature between 350° C. and 650° C., especially 400° C. to 450° C., and an $H_2$ load of 1–60 liters/g catalyst per hour. In the reduced molded bodies, the metal crystal size is in a range of $\leq 3$ nm. The fracture strength of the reduced air stabilized molded bodies in $>30N$, the specific pore volume is between 0.05 and 0.9 ml/g, and the BET surface area is between 80 and 400 $m^2/g$.

According to the second embodiment of this invention, a highly porous support is impregnated with a solution of the metal salt and an excess of the compound that decomposes slowly when heated in an aqueous medium with an increase in pH, preferably in a 1.5 to 3 molar excess, whereby the concentration of the metal in the solution is calculated so that the amount of metal in a the part of the solution filling the pores of the molded body constitutes 5 to 30 wt % of the finished catalyst based on MeO, whereby the support constitutes 70 to 95 wt %.

For both embodiments, all solvents whose boiling point is higher than the decomposition temperature of the compound that decomposes slowly on heating in solution with an increase in pH can be used. Both this compound and the metal salt are soluble in the solvent in the amounts described above. If urea is used in the especially preferred embodiment of this invention, then suitable solvents include, for example, water and ethylene glycol.

According to an especially preferred embodiment of this invention, the molded bodies are covered with the solution described above and left to stand for a time, preferably for more than 10 minutes and then are separated from the supernatant solution.

The wet molded bodies are then transferred to an open vessel equipped with a reflux condenser or a closed container and kept for a long period of time, preferably 8 to 60 hours, at a temperature higher than the decomposition temperature of the compound which decomposes slowly when heated in solution with an increase in pH. During this period of time, this compound decomposes and the metal is precipitated as a sparingly soluble compound. The resulting molded bodies are washed and then dried.

The dried molded bodies are either reduced immediately or they are first calcined. Calcination is generally performed at temperatures of more than 250° C., preferably at 300°–500° C., for a period of 2–10 hours. Reduction preferably takes place at a temperature between 350° C. and 650° C., most preferably 400°–450° C. with an $H_2$ load of 1–60 liters per g catalyst per hour.

The molded catalyst bodies described above are useful for hydrogenation of mono- or polyunsaturated organic compounds, especially for hydrogenation of aromatics. The molded catalyst bodies are also useful in methanization and oligomerization reactions.

This invention is illustrated by the following examples although it is in no way limited to them.

EXAMPLE 1

A suspension of 1946.6 g $Ni(NO_3)_2.6H_2O$, 1225.2 g urea and 1500 g pyrogenic silicic acid (BET surface area 150 $m^2/g$) in 40 liters of water is reacted while stirring at 100° C. under reflux conditions until the nickel content of the filtrate is $<10$ ppm. The reaction mass is then filtered. The filter cake is washed three times with hot water and is then transferred to a heated kneader where it is adjusted to an extruder moisture content (about 56 wt % water) while kneading continuously. The compound is extruded to strands with a diameter of 2 mm. The wet extrudates shrink to a diameter of 1.5 mm when they dry. After calcination at 400° C., they have the following properties:
NiO content: 25 wt %
BET surface area: 199 $m^2/g$
Specific pore volume: 0.83 ml/g
Fracture strength: 37N The dried extrudates are reduced in a stream of hydrogen at 400° C., yielding Ni crystals whose size is below the smallest size of 2.8 nm that can be calculated from X-ray diffraction measurements.

EXAMPLE 2

A suspension of 285 g $Cu(NO_3)_2.3H_2O$, 211.8 g urea and 175 g pyrogenic silicic acid (BET surface area 150 $m^2/g$) in 5 liters of water is reacted while stirring at 100° C. under reflux conditions until the copper content of the filtrate is $<10$ ppm and then the suspension is filtered. The filter cake is washed three times with hot water and then transferred to a heated kneader where it is adjusted to an extruder moisture content (about 56 wt % water) while kneading continuously. The compound is extruded to strands with a diameter of 2 mm. The wet extrudates shrink on drying to a diameter of 1.5 mm. After calcination at 450° C. they have the following properties:
CuO content: 37.5 wt %.
BET surface area: 390 $m^2/g$
Specific pore volume: 0.72 ml/g
Fracture strength: 35N.

The dried extrudates are reduced at 400° C. in a stream of hydrogen, yielding Cu crystals $<3.0$ nm in size.

EXAMPLE 3

A suspension of 295 g $Fe(NO_3)_3.9H_2O$, 134 g urea and 175 g pyrogenic silicic acid (BET surface area 150 $m^2/g$) in 5 liters of water is reacted at reflux conditions at 100° C. until the Fe content of the filtrate is $<10$ ppm and then the suspension is filtered. The filter cake is washed three time with hot water and then transferred to a heated kneader where it is adjusted to an extruder moisture content (about 56 wt % water) while kneading continuously. The compound is extruded to strands 2 mm in diameter. The wet extrudates shrink to a diameter of 1.5 mm on drying. After calcination at 400° C., they have the following properties:
$Fe_2O_3$ content: 25 wt %
BET surface area: 108 $m^2/g$
Specific pore volume: 0.86 ml/g
Fracture strength: 33N The dried extrudates are reduced at 400° C. in a stream of hydrogen, yielding Fe crystals whose size is smaller than the smallest size of 2.8 nm that can be calculated from X-ray diffraction measurements.

EXAMPLE 4

A suspension of 226.6 g Co(NO$_3$)$_2$.6H$_2$O, 140 g urea and 175 g pyrogenic silicic acid (BET surface area 150 m$^2$/g) in 5 liters of water is reacted under reflux conditions while stirring at 100° C. until the Co content of the filtrate is 10 ppm and then the suspension is filtered. The filter cake is washed three times with hot water and then transferred to a heated kneader where it is adjusted to an extruder moisture content (about 56 wt % H$_2$O) while kneading continuously. The compound is extruded to yield strands with a diameter of 2 mm. The wet extrudates shrink on drying to a diameter of 1.5 mm. After calcination at 400° C., they have the following properties;
CoO content: 25 wt %
BET surface area 238 m$^2$/g
Specific pore volume: 0.64 ml/g
Fracture strength: 36N The dried extrudates are then reduced in a stream of hydrogen at 400° C., yielding Co crystals whose size is smaller than the smallest size of 2.8 nm that can be calculated from X-ray diffraction measurement.

EXAMPLE 5

259.5 g Ni(NO$_3$)$_2$.6H$_2$O and 107.2 g urea are dissolved in enough water to yield a solution volume of 290 ml 100 g SiO$_2$ extrudates (diameter 1.5 mm) with a water uptake of 145 percent are covered with this solution, left to stand for 1 hour and then filtered. The impregnated extrudates are transferred to a flask equipped with a reflux condenser, heated in an oil bath at 90° C. and kept at this temperature for 24 hours. Then they are washed three times with hot water, dried and calcined for 4 hours at 400° C. They then have the following properties:
NiO content: 24.2 weight percent
BET surface area: 242 m$^2$/g
Specific pore volume: 0.70 ml/g
Fracture strength: 41N The dried extrudates are reduced at 400° C. in a stream of hydrogen, yielding Ni crystals that are smaller than the smallest size of 2.8 nm that can be calculated from X-ray diffraction measurements.

EXAMPLE 6 (COMPARISON)

The extrudates described in Example 5 are impregnated with the nickel nitrate solution described there except no urea is added, and then they are dried for 24 hours at 120° C. in a drying cabinet and calcined for 4 hours at 400° C., at which point they have the following properties:
NiO content: 25.2 weight percent
BET surface area: 235 m$^2$/g
Specific pore volume: 0.68 ml/g
Fracture strength: 31N The dried extrudates are reduced in a stream of hydrogen at 400° C., yielding Ni crystals 9.8 nm in size.

EXAMPLE 7 (APPLICATION)

To perform hydrogenation of toluene to methylcyclohexane in a trickle phase, 15 ml of the catalyst prepared according to Example 5 and diluted with glass beads are transferred to a tubular reactor. The reaction takes place at 30 bar and 110° C. for 70 hours. A mixture of 30 weight percent toluene and 70 weight percent methylcyclohexane is used as the feedstream material. The load (LHSV = liquid hourly space velocity) is 1 liter (toluene)/1 liter (catalyst) hour, and the hydrogen throughput amounts to 1450 liters per liter of toluene. The average conversion of toluene is thus 58.5 percent.

EXAMPLE 8 (COMPARISON)

The catalyst produced according to Example 6 is tested under the same conditions as those specified in Example 7. The average toluene conversion here amounts to 42.3 percent.

As shown by a comparison of Examples 5 and 6 or 7 and 8, the advantage of the catalyst according to this invention is the 30 percent higher strength and much smaller crystals than with the comparative catalyst. This latter feature results in an almost 40 percent higher conversion of toluene in the test reaction using the catalyst according to this invention in comparison with the reference catalyst.

What is claimed is:

1. Molded catalyst body which in a reduced state contains a metal of the ferrous group and/or copper on a support, obtained by reacting a compound that decomposes when heated slowly in solution with an increase in pH of the aqueous medium with a solution of a salt of a metal of the ferrous group and/or copper in the presence of a powdered suspended support in order to produce a precipitate of insoluble metal compound on the support, separating the precipitate together with the support from the solution and plasticizing and shaping it while still wet while heating, then drying/or calcining and reducing the compound wherein said molded catalyst body is characterized by the following features:
    (a) Metal content: about 5 to about 40 weight percent based on the total weight of the catalyst;
    (b) Metal-crystal size: ≦3 nm;
    (c) Volume of the pores having a diameter of 7.5 nm to 15 μm: 0.05 to 0.9 ml/g catalyst;
    (d) BET surface area: about 80 to about 400 m$^2$/g catalyst;
    (e) Fracture strength: >30N (based on a cylindrical molded body with a diameter of 1.5 nm and a length of 5 mm);
    (f) Bulk density: 250-350 g/liter.

2. Molded catalyst body according to claim 1, wherein the support is made of a powdered oxide or silicate.

3. Molded catalyst body according to claim 2, wherein the support is made of a powdered pyrogenic silicic acid.

4. Molded catalyst body according to claim 1 having the following pore diameter distribution:
    7.5 nm to 14 nm: 0 to 2 percent
    14 nm to 80 nm: 1 to 25 percent
    80 nm to 1.75 μm: 50 to 90 percent
    1.75 μm to 15 μm: 0 to 15 percent.

5. Molded catalyst body according to claim 1, characterized in that the compound which decomposes slowly when heated in solution with an increase in pH is ammonium carbonate or bicarbonate, urea, an amide, or an amine.

6. Molded catalyst body according to claim 5 wherein the amide is formamide, dimethylformamide, acetamide, or dimethylacetamide.

7. Molded catalyst body according to claim 5 wherein the amine is hexamethylenetetramine.

8. Molded catalyst body according to claim 1 obtained by decomposing a compound that decomposes at a temperature of >50° C., when heated in solution with an increase in pH, while the molded body is in a saturated solvent vapor atmosphere.

9. Molded catalyst body according to claim 8 wherein the decomposition temperature of the compound is >90° C.

10. Molded catalyst body according to claim 1 wherein the solvent has a boiling point higher than the decomposition temperature of the compound which decomposes with an increase in pH.

11. Molded catalyst body according to claim 1, characterized in that the heat is supplied in a heated mixer.

12. Molded catalyst body according to claim 1 obtained by agglomeration or extrusion.

13. Molded catalyst body that contains in a reduced state a metal of the ferrous group and/or copper on a support which is obtained by reacting a compound that decomposes slowly when heated in solution with an increase in pH with a solution of a salt of a metal of the ferrous group and/or copper in the pores of a porous molded support body in order to produce a precipitate of insoluble metal compounds in the pores of the molded support body, then separating the precipitate together with the molded support body from the solution, drying it and/or calcining it and reducing the metal compound wherein said molded catalyst body is characterized by the following features:
  (a) Metal content: about 5 to about 40 weight percent based on the total weight of the catalyst;
  (b) Metal-crystal size: $\leq 3$ nm;
  (c) Volume of the pores having a diameter of 7.5 nm to 15 $\mu$m; 0.05 to 0.9 ml/g catalyst;
  (d) BET surface area: about 80 to about 400 m$^2$/g catalyst;
  (e) Fracture strength: >30N (based on a cylindrical molded body with a diameter of 1.5 mm and a length of 5 mm;
  (f) Bulk density: 250–350 g/liter.

14. Molded catalyst body according to claim 13 having the following pore diameter distribution:
  7.5 nm to 14 nm: 0 to 2 percent
  14 nm to 80 nm: 1 to 25 percent
  80 nm to 1.75 $\mu$m: 50 to 90 percent
  1.75 m to 15 $\mu$m: 0 to 15 percent.

15. Molded catalyst body according to claim 13 characterized in that the compound which decomposes slowly when heated in solution with an increase in pH is ammonium carbonate or bicarbonate, urea, an amide or an amine.

16. Molded catalyst body according to claim 15 wherein the amide is formamide, dimethylformamide, acetamide or dimethylacetamide.

17. Molded catalyst body according to claim 15 wherein the amine is hexamethylenetetramine.

18. Molded catalyst body according to claim 13 obtained by decomposing a compound that decomposes at a temperature >50° C. when heated in solution with an increase in pH while the molded body is in a saturated solvent vapor atmosphere.

19. Molded catalyst body according to claim 18 wherein the decomposition temperature of the compound is >90° C.

20. Molded catalyst body according to claim 13 wherein the solvent has a boiling point higher than the decomposition temperature of the compound which decomposes with an increase in pH.

21. Molded catalyst body according toe claim 13 obtained by impregnating the support with excess solution.

22. Molded catalyst body according to claim 13, characterized in that the molded support body is impregnated by the pore-filling method, whereby the volume of the impregnating solution corresponds at most to the pore volume of the molded body.

23. Molded catalyst body according to claim 13 obtained by drying the wet molded catalyst body first at a temperature of $\geq 95$° C. for a period of $\geq 4$ hours and then calcining it at a temperature of $\geq 250$° C.

24. Molded catalyst body according to claim 13 in the form of pressed cylinders, tablets, pellets, wagon wheels, rings, or stars, or extruded solid strands, polylobed strands, hollow strands or honeycomb bodies.

* * * * *